(12) United States Patent
Stochniol et al.

(10) Patent No.: US 10,227,279 B2
(45) Date of Patent: Mar. 12, 2019

(54) DEHYDROGENATION OF LPG OR NGL AND FLEXIBLE UTILIZATION OF THE OLEFINS THUS OBTAINED

(71) Applicant: Evonik Degussa GmbH, Essen (DE)

(72) Inventors: Guido Stochniol, Haltern am See (DE); Andreas Wolff, Recklinghausen (DE); Stephan Peitz, Oer-Erkenschwick (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/689,322

(22) Filed: Aug. 29, 2017

(65) Prior Publication Data

US 2018/0072647 A1 Mar. 15, 2018

(30) Foreign Application Priority Data

Sep. 12, 2016 (EP) .................... 16188267

(51) Int. Cl.
| | |
|---|---|
| *C07C 2/24* | (2006.01) |
| *C07C 5/00* | (2006.01) |
| *C07C 45/50* | (2006.01) |
| *C07C 5/03* | (2006.01) |
| *C07C 5/327* | (2006.01) |
| *C07C 5/333* | (2006.01) |
| *C07C 5/48* | (2006.01) |

(52) U.S. Cl.
CPC ............ *C07C 45/50* (2013.01); *C07C 2/24* (2013.01); *C07C 5/03* (2013.01); *C07C 5/327* (2013.01); *C07C 5/333* (2013.01); *C07C 5/48* (2013.01); *C07C 2521/12* (2013.01); *C07C 2523/755* (2013.01)

(58) Field of Classification Search
CPC .. C07C 2/24; C07C 5/03; C07C 5/327; C07C 45/50
See application file for complete search history.

(56) References Cited

U.S. PATENT DOCUMENTS

| | | | |
|---|---|---|---|
| 2,581,228 | A | 1/1952 | Bailey et al. |
| 5,912,191 | A | 6/1999 | Nierlich et al. |
| 5,998,685 | A | 12/1999 | Nierlich et al. |
| 7,939,597 | B2 | 5/2011 | Bub et al. |
| 8,198,481 | B2 | 6/2012 | Kuppinger et al. |
| 8,258,249 | B2 | 9/2012 | Bub et al. |
| 8,293,941 | B2 | 10/2012 | Kuppinger et al. |
| 8,481,784 | B2 | 7/2013 | Kuppinger et al. |
| 8,524,945 | B2 | 9/2013 | Stochniol et al. |
| 8,895,683 | B2 | 11/2014 | Kuppinger et al. |
| 9,206,105 | B2 | 12/2015 | Christiansen et al. |
| 9,272,973 | B2 | 3/2016 | Fridag et al. |
| 9,409,844 | B2 | 8/2016 | Christiansen et al. |
| 9,499,463 | B2 | 11/2016 | Christiansen et al. |
| 9,556,096 | B2 | 1/2017 | Christiansen et al. |
| 9,682,898 | B2 | 6/2017 | Peitz et al. |
| 2006/0122436 | A1 | 6/2006 | Schindler et al. |
| 2006/0276334 | A1 | 12/2006 | Balduf et al. |
| 2009/0068440 | A1 | 3/2009 | Bub et al. |
| 2011/0282092 | A1 | 11/2011 | Godsmark et al. |
| 2016/0002136 | A1 | 1/2016 | Lueken et al. |
| 2016/0257630 | A1 | 9/2016 | Stochniol et al. |

FOREIGN PATENT DOCUMENTS

| | | |
|---|---|---|
| DE | 10251262 A1 | 5/2004 |
| DE | 102008007081 A1 | 8/2009 |
| EP | 0820973 A1 | 1/1998 |
| EP | 0820974 B1 | 12/2000 |
| WO | 2014056732 A1 | 4/2014 |
| WO | 2014131623 A1 | 9/2014 |
| WO | 2014207034 A1 | 12/2014 |

OTHER PUBLICATIONS

U.S. Appl. No. 15/827,193, filed Nov. 30, 2017.
European Search Report dated Mar. 17, 2017 in EP 16 188 267.5 (6 pages).
Ebinger et al., Natural Gas Liquids, Brookings Energy Security Initiative, copyright Mar. 2013, web page, www.brookings.edu/research/natural-gas-liguids-the-other-driver-of-the-u-s-oil-and-gas-supply-resurgence/ (16 pages).
Reeker et al., U.S. Appl. No. 15/605,170, filed May 25, 2017.
Stochniol et al., U.S. Appl. No. 15/623,631, filed Jun. 15, 2017.

*Primary Examiner* — Sikarl A Witherspoon
(74) *Attorney, Agent, or Firm* — Philip P. McCann; Nexsen Pruet, PLLC

(57) ABSTRACT

The object of the invention is to specify a process with which both $C_5$ and $C_9$ aldehydes can be produced economically. Here, the process should be able to to be supplied with the lowest possible dependence on raw material suppliers and also should be able to react flexibly to fluctuations in demand with respect to $C_5$ and $C_9$ aldehydes. The use of resources should also be optimized. The process proposed uses LPG or NGL as raw material. The process according to the invention essentially differs from known LPG-based processes in that the intermediate obtained, after dehydrogenation and removal of by-products, is divided into two portions. C9 aldehyde is produced from the first portion by oligomerization and hydroformylation while C5 aldehyde is obtained by hydroformylation of the second portion. This has the critical advantage that it is possible to divide the intermediate flexibly into the two portions so that either more $C_5$ or more $C_9$ aldehydes can be produced depending on the respective demand.

20 Claims, 5 Drawing Sheets

DEHYDROGENATION OF LPG OR NGL AND FLEXIBLE UTILIZATION OF THE OLEFINS THUS OBTAINED

This application claims the benefit of European Application No. 16188267.5 filed on Sep. 12, 2016, the disclosure of which is expressly incorporated herein by reference.

BACKGROUND

The invention is concerned with the issue of how alternative raw materials may be exploited in the production of $C_4$-based aldehydes.

Hydrocarbons are chemical compounds which consist exclusively of carbon and hydrogen. Alkenes (synonym: olefins) are hydrocarbons which have a C=C double bond in the molecule. Alkanes (synonym: paraffins), on the other hand, are hydrocarbons which have only single bonds. They are therefore also referred to as saturated. Due to the different bond types, alkenes are significantly more reactive than alkanes. Therefore, alkenes are chemically more utilizable and correspondingly more valuable than alkanes.

In organic chemistry, hydrocarbons are frequently designated according to the number of carbon atoms which they have per molecule, in that the respective class of substances is preceded by the prefix $C_n$. "n" is the respective number of carbon atoms in a molecule. Thus, $C_4$ olefins are substances from the class of alkenes having four carbon atoms. $C_8$ olefins correspondingly have eight carbon atoms per molecule. Where the prefix $C_{n+}$ is used hereinafter, it refers to a class of substances which have more than n carbon atoms per molecule. A $C_{4+}$ olefin accordingly has at least five carbon atoms.

Due to the different arrangement and linking possibilities of the carbon and hydrogen atoms, several isomers, which have the same number of carbon atoms, exist within the substance classes discussed here. For instance, two alkanes exist having four carbon atoms in each case, namely n-butane and isobutane. Since the variety of combinations is greater for the alkenes, even more isomers are possible. For instance, in total four olefins having four carbon atoms exist, namely isobutene, 1-butene, cis-2-butene and trans-2-butene. The three linear butenes, 1-butene, cis-2-butene and trans-2-butene, are often referred to collectively as n-butene. For the $C_3$ hydrocarbons in contrast, there is only one isomer in each case, namely the alkane having three carbon atoms, propane, and the $C_3$ alkene propene. In the longer-chain $C_{5+}$ hydrocarbons, the multiplicity of isomers increases markedly. Despite the identical number of carbon atoms, isomers have different properties which are relevant for their industrial use.

The aldehyde substance class comprises substances which, due to their high reactivity, are used as starting substance for the preparation of various speciality chemicals such as lubricants, plasticizers and detergents. It is also possible to use aldehydes as fragrances.

Aldehydes are produced from alkenes and synthesis gas, i.e. a mixture of hydrogen and carbon monoxide. This procedure is called hydroformylation or oxo reaction. In this case, the number of carbon atoms increases by one. In this manner, a $C_5$ aldehyde (pentanal) is formed from a $C_4$ olefin by hydroformylation.

Aldehydes having a higher carbon atom number can be generated by either reacting lower aldehydes with one another to give higher aldehydes (aldol condensation) or reacting olefins only with themselves (oligomerization) and then hydroformylating the olefin oligomers obtained in this case.

For instance, a $C_{10}$ aldehyde may be obtained by hydroformylating a $C_4$ olefin to give the $C_5$ aldehyde and this is then reacted with itself by aldol condensation to give the $C_{10}$ aldehyde (decanal). $C_9$ aldehyde may also be prepared from $C_4$ olefin if it is firstly converted by oligomerization to a $C_8$ olefin and this is subsequently hydroformylated to the $C_9$ aldehyde.

Aldehydes having both five and nine carbon atoms can thus be prepared from $C_4$ olefins; also $C_{10}$ aldehydes by subsequent aldol condensation of the pentanals. This is also thus carried out in industrial practice in complexly connected compound installations:

DE102008007081A1 describes a process for utilizing $C_4$ mixtures comprising at least 1-butene, isobutene, butanes, 2-butenes and polyunsaturated $C_4$ hydrocarbons. It is mentioned in passing that $C_9$, $C_{13}$ and $C_{17}$ aldehydes can be prepared from the separated n-butene via oligomerization and hydroformylation, while the high-purity 1-butene also obtained is suitable, inter alia, for preparing valeraldehyde.

This process uses as raw material source so-called C4 cuts which originate as "crack C4" from steamcrackers or as "FCC C4" from fluidized-catalytic crackers. Such crackers are substantially charged with naphtha or VGO (vacuum gas oil) which originate in turn from the distillation of crude oil. Since crack C4 and FCC C4 are in the added-value chain of the petrochemical products of crack processes, the prices for these raw materials are correspondingly volatile owing to their dependence on the price of oil. Moreover, the availability of high-value crack C4 has been steadily falling since the operation of the steam crackers is optimized towards the production of the $C_2$ and $C_3$ olefins ethene and propene to the detriment of the $C_4$ yield. A disadvantage of the process described in DE102008007081A1 can thus be considered to be its dependence on a specific raw material basis.

A further disadvantage of this process is that the n-butane and isobutane, sometimes present in significant amounts in $C_4$ mixtures used, exhibit inert behaviour in the process and are therefore not materially utilized. In the interests of the $CO_2$ balance of the process, as far as possible all carbon atoms present in the feedstock mixture should be utilized in a chemically sustainable manner and if at all possible they should not be incinerated. The resource efficiency of the process known from DE102008007081A1 is therefore capable of improvement.

Another raw material basis uses the process described in EP0820974B1. Processed therein are so-called "field butanes" which are $C_4$ fractions of the "wet" components of natural gas and the gases accompanying mineral oil, which are separated from the gases by drying and cooling to about $-30°$ C. in liquid form. Low-temperature distillation gives the field butanes whose composition fluctuates depending on the deposit, but which generally comprise about 30% isobutane and about 65% n-butane. Further constituents are generally about 2% hydrocarbons having fewer than four carbon atoms and about 3% $C_{4+}$ hydrocarbons.

The field butanes are dehydrogenated such that a mixture is formed comprising, inter alia, n-butene and isobutene. This mixture is worked-up and the n-butene separated here is converted by oligomerization to substantially $C_8$ olefins and additionally $C_{12}$ olefins. The $C_8$ and $C_{12}$ olefins are converted by hydroformylation and hydrogenation into $C_9$ and $C_{13}$ alcohols, and therefore corresponding aldehydes must be present prior to hydrogenation. $C_5$ aldehydes are not produced however. A disadvantage of this process is that a continuous turnover of $C_9$ and $C_{13}$ alcohols is required in order to be able to utilize the field butanes in question. Since field butanes can hardly be traded otherwise, the purchase of field butanes is possible only via long-term continuous supply contracts. Therefore, there is a dependence on a specific raw material here also which is enhanced by buyer dependence, however.

With respect to EP0820974B1, there is therefore the need, through technical measures, to have a greater freedom in the choice of raw material suppliers and to be able to react to fluctuating demand of the buyers.

Another raw material source for aldehyde preparation is in turn exploited in US2006/0122436A1. The alkanes used in this publication originate from LPG.

LPG (liquefied petroleum gas) is a common international trade name for a liquid mixture of $C_3$ and/or $C_4$ hydrocarbons which is obtained as a by-product in the recovery of mineral oil or natural gas from its deposit or in the work-up of crude oil in the refinery. The precise composition of LPG depends significantly on its origin; its essential constituents are usually propane and butanes.

There exists a global ecosystem based on LPG which promotes, transports and markets this product mainly as propellant and fuel.

A comprehensive introduction to LPG technology and economics based thereon is found in:

Thompson, S. M., Robertson, G. and Johnson, E.: Liquefied Petroleum Gas. Ullmann's Encyclopedia of Industrial Chemistry. Published Online: 15 Jul. 2011. DOI: 10.1002/14356007.a15_347.pub2

US2006/0122436A1 discloses, then, two routes as to how aldehydes or alcohols can be prepared from LPG; cf. the claims 1 and 7 therein.

In the first process according to claim 1, $C_n$ aldehydes are produced from $C_{n-1}$ alkanes. n in this case is an integer from 4 to 20. Accordingly, in the case of n=5, $C_5$ aldehydes are prepared from $C_4$ alkanes, and, in the case of n=9, $C_9$ aldehydes are prepared from $C_8$ alkanes. This is accomplished, for example in the case of $C_4$ alkanes, by dehydrogenating the butane present in the LPG initially to butene and secondary constituents. After removal of the secondary constituents, the butenes are hydroformylated to pentanals. The pentanals are converted by aldol condensation into decanals.

In the second process, the corresponding $C_{2n}$ and $C_{2n-1}$ alcohols are prepared from $C_{n-1}$ alkanes via $C_n$ aldehydes, $C_{2n}$ aldehydes and $C_{2n-1}$ aldehydes. In the case of n=5, $C_5$, $C_9$ and $C_{10}$ alcohols are accordingly produced from $C_4$ alkanes. This is accomplished in principle exactly as in the first process but with the difference that the hydroformylation, for example of the $C_4$ alkenes, to give the pentanals takes place explicity only under partial conversion; cf. step 7c. The pentanals are separated from the unreacted butenes (step 7d) and aldol-condensed to give decanals, in order to subsequently prepare decanols by means of catalytic hydrogenation (steps 7e and 7f). The unreacted butenes are subjected to an oligomerization (step 7g) such that $C_8$ olefins are obtained. These are then hydroformylated to give $C_9$ aldehydes (step 7h) and subsequently hydrogenated to give $C_9$ alcohols (step 7i).

A conceptual disadvantage of this process is that the oligomerization (from $C_{n-1}$ to $C_{2n-2}$) and the subsequent second hydroformylation of the oligomers (from $C_{2n-2}$ to $C_{2n-1}$) is arranged downstream of the first hydroformylation (from $C_{n-1}$ to $C_n$), the two hydroformylation steps thus being connected serially (in series). This means that the second hydroformylation is provided as a "residue utilization" of the first hydroformylation and ultimately converts the oligomers of the $C_{n-1}$ alkenes which the first hydroformylation did not convert. The supply to the second hydroformylation with raw material is accomplished consequently by adjusting the degree of the partial conversion of the first hydroformylation.

In a market situation in which significantly more $C_9$ aldehydes than $C_5$ or $C_{10}$ aldehydes are in demand, the conversion of the first hydroformylation (which serves the $C_5$ and $C_{10}$ market) has to be very significantly shut down in the compound concept described in US2006/0122436A1, in order to leave sufficient unreacted butene for the second hydroformylation (which makes the desired $C_9$). This means that the first hydroformylation has to be conducted in a very unfavorable operating state and therefore operates very inefficiently.

A further disadvantage of the serial connection of dehydrogenation, first hydroformylation, oligomerization and second hydroformylation is due to the fact that commercially available plants for the dehydrogenation of alkanes, which is mentioned in paragraph [0022] of US2006/0122436A1, are operated generally in the context of naphtha crackers such that these processes are all designed and optimized on a throughput in the petrochemical dimension. For instance, the capacity of a propane dehydrogenation according to the STAR® process is about 500 000 t/a of propylene. Propane dehydrogenations by the CATOFIN® process are even designed for 850 000 t/a. These are scales which differ very markedly from those of industrially operated hydroformylation; thus the capacity of an oxo plant is typically only 100 000 t/a. Even if two large 250 kt/a oxo plants were capable of processing the alkenes supplied from a 500 kt/a dehydrogenation, the first hydroformylation would still have to be additionally oversized in order to be able to loop a correspondingly large amount of unreacted alkene for the second oxo plant in the case of partial loading. Using this process layout, the dehydrogenation is therefore too large or the hydroformylations are too small in order to be able to operate the entire process economically. A remedy here would offer only a costly specific development of an unusually small dehydrogenation or the possibility to use alkene produced in excess in some other way than for aldehyde production. In this respect, once again new buyer dependencies are created.

SUMMARY

Following all this, there exists still a requirement to specify a process with which both $C_5$ and $C_9$ aldehydes can be produced economically. Here, the process should be able to be supplied with the lowest possible dependence on raw material suppliers and also should be able to react flexibly to fluctuations in demand with respect to $C_5$ and $C_9$ aldehydes. The use of resources for the process should also be optimized.

DETAILED DESCRIPTION

Figure 1:
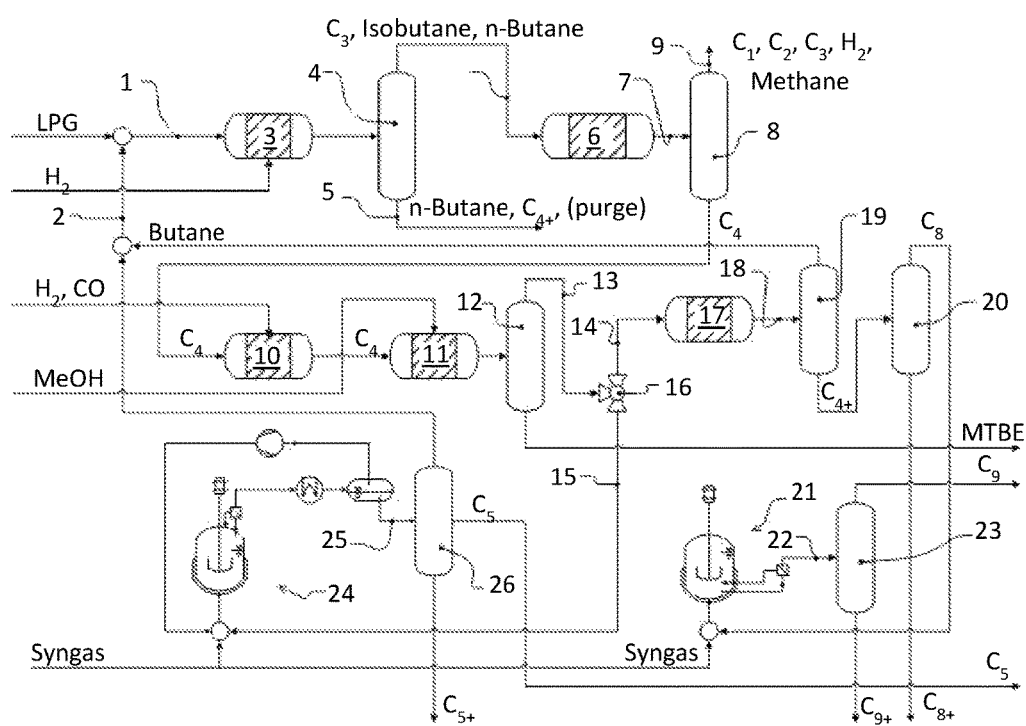
FIG. 1: Basic implementation of the process.

This object is achieved by a process for the flexible preparation of aldehydes having five and nine carbon atoms comprising the following steps:
- a) providing a liquid mixture, called LPG or NGL (liquefied petroleum gas or natural gas liquids), which comprises specifically a main component selected from the group consisting of propane, isobutane and n-butane, and at least one secondary component selected from the group consisting of propane, isobutane, n-butane, propene, isobutene and n-butene, with the proviso that the main component selected and the secondary component selected are not identical, and that the mixture has the following composition including the limit values which add up to 100% by weight:
   propane: 0 wt % to 50 wt %;
   isobutane: 0 wt % to 100 wt %;
   n-butane: 0 wt % to 100 wt %;
   propene: 0 wt % to 3 wt %;
   isobutene: 0 wt % to 10 wt %;
   n-butene: 0 wt % to 15 wt %;
   sum of other substances: 0 wt % to 5 wt %;
- b) mixing a feed mixture using the LPG or NGL;
- c) in the case that the feed mixture comprises more than 1.0% by weight unsaturated hydrocarbons: reducing the content of unsaturated hydrocarbons in the feed mixture to a value below 1.0% by weight by subjecting the feed mixture to a hydrogenation;
- d) optionally: reducing the n-butane content of the feedstock mixture by distillation of the feed mixture to obtain a bottoms fraction comprising n-butane, wherein the proportion of n-butane in the bottoms fraction comprising n-butane is greater than the proportion of n-butane in the distilled feed mixture;
- e) dehydrogenating the feed mixture to obtain at least one dehydrogenation mixture,
- f) obtaining a $C_4$ fraction from the dehydrogenation mixture, wherein the $C_4$ fraction has the following composition including the limit values which add up to 100% by weight:
   1,3-butadiene: 1 wt % to 5 wt %;
   isobutene: 20 wt % to 50 wt %;
   n-butene: 20 wt % to 50 wt %;
   sum of isobutane and n-butane: 2 wt % to 60 wt %;
   sum of other substances: 0 wt % to 1 wt %;
- g) at least partial removal of 1,3-butadiene and isobutene from the $C_4$ fraction to obtain an intermediate which has the following composition including the limit values which add up to 100% by weight:
   1,3-butadiene: 0 wt % to 500 ppm by weight;
   isobutene: 0 wt % to 2 wt %;
   n-butene: 30 wt % to 55 wt %;
   sum of isobutane and n-butane: 45 wt % to 70 wt %;
   sum of other substances: 0 wt % to 500 ppm by weight;
- h) dividing the intermediate into a first portion and a second portion in a splitter;
- i) optionally reducing the isobutane content of the first portion of the intermediate by distillation of the first portion of the intermediate to obtain a bottoms fraction comprising isobutane, wherein the proportion of isobutane in the bottoms fraction comprising isobutane is greater than the proportion of isobutane in the first portion of the intermediate distilled and using the bottoms fraction comprising isobutane to increase the isobutane content of the feed mixture in which the bottoms fraction comprising isobutane is added to the feed mixture or is used when mixing the feed mixture;
- j) subjecting the first portion of the intermediate to an oligomerization in the presence of a solid catalyst comprising amorphous silica/alumina and at least 15% by weight nickel, whereby an oligomer is obtained comprising olefins having eight carbon atoms and butane,
- k) separating butane from the oligomer and using the butane separated when mixing the feed mixture;
- l) separating olefins having eight carbon atoms from the oligomer and pressurizing the separated olefins having eight carbon atoms with synthesis gas for the purpose of carrying out a first hydroformylation to obtain a first hydroformylation mixture comprising at least aldehydes having nine carbon atoms;
- m) separating a first target fraction comprising aldehydes having nine carbon atoms from the first hydroformylation mixture;
- n) pressurizing the second portion of the intermediate with synthesis gas for the purpose of carrying out a second hydroformylation to obtain a second hydroformylation mixture comprising at least aldehydes having five carbon atoms and also butane;
- o) separating butane from the second hydroformylation mixture and using the butane separated when mixing the feed mixture;
- p) separating a second target fraction comprising aldehydes having five carbon atoms from the second hydroformylation mixture.

The invention provides such a process.

The process according to the invention uses either LPG or NGL as raw material. Therefore, it can be provided via the open LPG market from many sources and from different suppliers. LPG is also transported in tankers and can therefore be supplied in the required amounts at sites with ports. Dependence on a single cracker is therefore no longer applicable.

Alternatively, the process can be charged with NGL (natural gas liquids). NGL is obtained from some natural gas fields, particularly in unconventional extraction. NGL comprises hydrocarbons having two to five carbon atoms. LPG from natural gas can therefore be considered as a partial fraction of NGL. The NGL market is currently not yet as highly developed as the LPG market but is expected to grow in the future:

Charles K. Ebinger and Govinda Avasarala: Natural Gas Liquids. https://www.brookings.edu/research/natural-gas-liquids-the-other-driver-of-the-u-s-oil-and-gas-supply-resurgence/

In the context of the invention, both LPG and NGL are understood to mean a mixture which satisfies the following specification:
   propane: 0 wt % to 50 wt %;
   isobutane: 0 wt % to 100 wt %;
   n-butane: 0 wt % to 100 wt %;
   propene: 0 wt % to 3 wt %;
   isobutene: 0 wt % to 10 wt %;
   n-butene: 0 wt % to 15 wt %;
   sum of other substances: 0 wt % to 5 wt %;

The percentage proportions of the substances present obviously add up to 100%. The limits specified should be understood as part of the range of values (mathematically: closed interval). LPG or NGL is however never a pure substance but always comprises specifically a main component and a secondary component or two or more secondary components. Only propane, isobutane and n-butane are suitable as main components. Secondary components may be all substances listed above with the exception of the other substances. A substance selected as main component cannot logically be simultaneously a secondary component.

From an economic perspective, it is also an important feature that LPG is formed by liquefaction of by-products obtained in the extraction of mineral oil or natural gas or in refining crude oil and that it is traded liquefied via an individual supply chain.

The process according to the invention may optionally process such types of LPG, which comprise comparatively low or comparatively high levels of propane. The process layout therefore differs in the details.

A low-propane LPG has the following specification:
propane: 0 wt % to 3 wt %;
isobutane: 20 wt % to 80 wt %;
n-butane: 20 wt % to 80 wt %;
propene: 0 wt % to 3 wt %;
isobutene: 0 wt % to 10 wt %;
n-butene: 0 wt % to 15 wt %;
sum of other substances: 0 wt % to 5 wt %.

An LPG type comprising a lot of propane has the following specification:
propane: 10 wt % to 40 wt %;
isobutane: 15 wt % to 85 wt %;
n-butane: 15 wt % to 85 wt %;
propene: 0 wt % to 3 wt %;
isobutene: 3 wt % to 10 wt %;
n-butene: 2 wt % to 15 wt %;
sum of other substances: 0 wt % to 5 wt %.

Preferably, a low-propane LPG is used whose main component is accordingly isobutane or n-butane.

Alternatively, the process can be carried out with NGL (natural gas liquids) as raw material. NGL is a mixture of hydrocarbons having two to five carbon atoms which is obtained in the extraction of natural gas from some deposits when the dry portion of the natural gas (the methane) is removed.

Typically, NGL has the following composition that adds up to 100% by weight:
ethane: 0 wt % to 2 wt %;
propane: 0 wt % to 50 wt %;
isobutane: 0 wt % to 100 wt %;
n-butane: 0 wt % to 100 wt %;
propene: 0 wt % to 3 wt %;
isobutene: 0 wt % to 10 wt %;
n-butene: 0 wt % to 15 wt %;
pentane: 0 wt % to 2 wt %;
sum of other substances: 0 wt % to 1 wt %.

An advantage of NGL is that it is produced independently of mineral oil.

The process according to the invention differs technologically from the LPG-based process known from US 2006/0122436 A1 essentially in that the intermediate obtained, after dehydrogenation and removal of by-products, is divided into two portions prior to hydroformylation. A $C_9$ aldehyde is produced from the first portion by oligomerization and hydroformylation while $C_5$ aldehyde is obtained by hydroformylation of the second portion. By contrast US 2006/0122436 A1 does not provide such a division prior to the hydroformylation, but rather, in certain cases, only that a separation of the $C_n$ aldehydes can take place after the (first) hydroformylation and the remaining $C_{n-1}$ alkenes can be oligomerized, hydroformylated and hydrogenated in sequence in order to obtain $C_{2n-1}$ alcohols.

The first and second hydroformylation are therefore arranged in parallel according to the invention and not serially. This has the critical advantage that it is possible to divide the intermediate flexibly into the two portions so that either more $C_5$ or more $C_9$ aldehydes can be produced depending on the respective demand.

A preferred embodiment of the process is therefore characterized in that the intermediate is divided into the first portion and the second portion considering the changing need over time for aldehyde having nine carbon atoms and aldehyde having five carbon atoms in such a way that the ratio of the first portion to the second portion changes analogously with time to the change over time of the ratio of the need for aldehyde having nine carbon atoms to the need for aldehyde having five carbon atoms.

The portions can be divided in accordance with the invention in a splitter, a comparatively simple valve which quantitatively divides the intermediate using a simple slide movement without a substance separation being performed. In comparison to the substance separation (i.e. hydroformylation of $C_{n-1}$ to $C_n$) operated in US2006/0122436A1, the conversion of the first oxo plant thus does not need to be controlled in a complex manner and the $C_4$ hydroformylation also does not have to assume any inefficient operational state in the case of high $C_9$ demand.

In a notable development of the process, the oligomerization is only conducted with partial conversion. The proportion of the partial conversion may be unchangeable over time. The partial conversion has a positive effect on the isomer distribution in the oligomer which is particularly of advantage when the intermediate subjected to the oligomerization comprises a low proportion of 1-butene. This effect is described in detail in WO2014/207034A1.

Moreover, the partial conversion also provides a further advantage: it makes it possible to remove the heat of reaction of the highly exothermic oligomerization from the reaction zone primarily with the oligomer. Preferably, more than 60% up to at most 90% of the heat of reaction resulting from the oligomerization should be removed from the reaction zone with the oligomer. Since the conversion is not complete, the oligomer still comprises sufficient unreacted olefin which can be used as heat transfer medium. In addition, not too much heat of reaction is formed since the mass introduced into the reaction zone is only partially converted. The heat removal via the oligomer and the limited conversion renders heat removal via an external cooling medium dispensable; the investment and operating costs of the reactor are thereby reduced. Oligomerization without external cooling corresponds to a part-adiabatic reaction regime.

Particularly preferably, even more than 90% up to at most 100% of the heat of reaction resulting from the oligomerization is removed from the reaction zone with the oligomer. This then corresponds to an adiabatic reaction regime.

According to step g) of the process, 1,3-butadiene and isobutene are at least partially removed prior to the hydroformylation such that the intermediate comprises at most 500 ppm by weight 1,3-butadiene and at most 2% by weight isobutene. These two substances are preferably removed completely such that the intermediate is free from 1,3-butadiene and isobutene. The reason for the removal of butadiene is that 1,3-butadiene permanently damages the oligomerization catalyst. The 1,3-butadiene is removed by selective hydrogenation; see also DE102008007081A1, EP0820974B1 and US2006/0122436A1.

Isobutene is removed since this branched olefin forms in turn branched aldehydes in the hydroformylation which has a negative effect on the product properties of the plasticizers subsequently produced from the aldehydes. It is therefore to be expected that the present process affords a different product quality to that described in US2006/0122436A1, since the isobutene therein is not separately removed but is fed explicitly into the hydroformylation.

The distillative removal of isobutene from a mixture with other $C_4$ alkenes and $C_4$ alkanes is not trivial since the differences in boiling points are very small. This problem is solved by reacting the isobutene selectively with methanol or another alcohol to give a high-boiling ether which can be removed more simply by distillation. A preferred development of the process therefore provides that, before or after carrying out the selective hydrogenation, the isobutene present in the $C_4$ fraction is reacted with an alcohol at least partially to give a corresponding ether and the ether formed in this case is at least partially removed by distillation. A suitable alcohol is preferably methanol which is reacted with isobutene to give methyl tert-butyl ether (MTBE). The removal of isobutene via MTBE synthesis has proven to be industrially useful. Details regarding MTBE technology for removing isobutene are set out in DE102008007081A1.

Instead of methanol, it is also possible to use ethanol as alcohol which forms ethyl tert-butyl ether (ETBE).

To arrange the removal of isobutene prior to the removal of butadiene makes sense energetically. If the catalyst used in the ether synthesis reacts sensitively to 1,3-butadiene however, the selective hydrogenation should be arranged prior to the ether synthesis.

A particular embodiment of the process provides that it is not fed at all exclusively with LPG or NGL but that additionally isobutane and/or n-butane is used when mixing the feed mixture, which does not originate from the LPG or NGL provided nor from the oligomer or from the second hydroformylation mixture.

The additional isobutane and/or n-butane in question is, as is the case in LPG or NGL, an external raw material which is fed externally. (The butane from the oligomer and from the second hydroformylation mixture are in contrast intra-process circulating substances.)

The idea behind this is to use the present process for "residue utilization" of streams containing otherwise not further chemically usable isobutane and/or n-butane.

Such streams remain at the end of the value addition chain of a conventional $C_4$ line (as disclosed in DE102008007081A1), and can no longer be chemically utilized due to the low reactivity of the alkanes remaining. They are instead used thermally or physically, more precisely burnt or used as propellant in spray cans.

By feeding such butane streams into the present process, the material efficiency of the overall operation may be increased since just these butanes are henceforth utilized chemically, specifically dehydrogenated.

It should be pointed out in this context that the dehydrogenation of residual alkanes without adding LPG or NGL is not economically viable, since the dehydrogenation in process engineering terms is very complex and also energy intensive. In addition, the differences in order of magnitude referred to above occur.

The concept to use the present process for residue utilization is accordingly based on the understanding that a further raw material firstly has to be purchased (namely LPG or NGL) in order to be able to utilize economically a residue (external isobutane and/or n-butane) already present.

Depending on the compound situation it may even be possible, when mixing the feed mixture in terms of quantity, to add more external butane than LPG or NGL.

The technology for dehydrogenating alkanes differentiates oxidative processes and non-oxidative processes. In oxidative dehydrogenation, an oxidizing agent such as oxygen or air is supplied to the alkane mixture in order to assure the heat requirement of the strongly endothermic dehydrogenation at least partially from the oxidation of the liberated hydrogen. In non-oxidative dehydrogenation, however, the addition of oxidizing agents is omitted and instead the heat required is introduced into the reactor externally, for example by heating with a fuel gas (usually methane, natural gas, cracking gases from the dehydrogenation process and optionally partly admixing hydrogen formed in the dehydrogenation). Both process variants differ significantly in the composition of the dehydrogenation mixture. A detailed discourse on common dehydrogenation technology can be found in US2006/0122436A1.

Oxidative dehydrogenation is advised by the specification. In contrast, it is preferable here that the dehydrogenation is effected at least partially without addition of an oxidizing agent—i.e. non-oxidatively. The reason for this is that non-oxidative dehydrogenation is more selective, additionally the hydrogen released, after separation and purification, may also be used for the hydrogenations provided in the process, by means of pressure swing absorption for example. During an oxidative dehydrogenation the hydrogen released is immediately burnt again with the purpose here to shift the equilibrium to the olefins formed according to Le Chatelier's principle.

The wording "at least partially without addition of an oxidizing agent" considers the circumstance that some commercially available non-oxidative dehydrogenations provide a hydrogen feed at the start of their reaction zone or immediately prior thereto.

The simplest possibility in process engineering terms of intergrating the dehydrogenation into the process is to dehydrogenate the $C_3$ and $C_4$ alkanes simultaneously and at the same site. The corresponding embodiment of the process accordingly provides that the dehydrogenation of the feed mixture is conducted in a reaction zone, and that the alkanes having three and four carbon atoms present in the feed mixture are dehydrogenated together in the same reaction zone.

The "reaction zone" in this context is the site at which the dehydrogenation takes place. In the simplest case, it is exactly one reactor. However, it is also possible to provide several reactors connected in parallel or in series. The totality of these reactors thus interconnected then forms the reaction zone. In the combined dehydrogenation of propane and butane in the same reaction zone, both alkanes are dehydrogenated under the same reaction conditions and over the same catalyst.

This naturally requires that the dehydrogenation of the $C_3$ and $C_4$ alkanes is accomplished simultaneously over the same catalyst. This is generally the case but the efficiency of the mixed dehydrogenation is limited and more undesired by-products are formed. Therefore, it is more efficient to dehydrogenate propane and butane separately.

The associated embodiment of the process accordingly provides that the dehydrogenation of the feed mixture is conducted in at least two reaction zones, wherein alkanes having three carbon atoms present in the feed mixture are dehydrogenated in the first reaction zone and wherein alkanes having four carbon atoms present in the feed mixture are dehydrogenated in the second reaction zone.

In process engineering terms, the separate dehydrogenation in dedicated reaction zones is more complicated than a mixed dehydrogenation but more efficient in material terms. It is decided in the individual case which variant is the more economically viable. An important deciding criterion will be the composition of the LPG delivered: If the plant is charged exclusively with low-$C_3$ LPG, the installation of dedicated reaction zones makes no sense.

In principle, it is also conceivable to select a variant in which three dedicated reaction zones are operated, a first for propane, a second for n-butane and a third for isobutane.

In addition, it is also possible to provide a first reaction zone for the mixed dehydrogenation of isobutane and propane and a further reaction zone for the dedicated dehydrogenation of n-butane. This makes particular sense if a column for separating n-butane and isobutane is installed. Using such a column, optional process step d) is effected, i.e. the reduction of the n-butane content of the feedstock mixture. A high-boiler fraction is obtained at the bottom thereof which is particularly rich in n-butane. If no other utilization possibility for these high boilers exist, the bottoms fraction of the column for separating n-butane and isobutane can be introduced partially or completely into a further reaction zone for dehydrogenating n-butane. The corresponding process variant is therefore characterized in that a further reaction zone is provided in which the distilled feed mixture is not dehydrogenated whereas the bottoms fraction comprising n-butene is subjected to a dehydrogenation in the further reaction zone. This process variant presupposes the implementation of step d).

It remains to be mentioned that the dedicated dehydrogenation in the limited extent will always represent a mixed dehydrogenation since the distillation columns, which perform the fractionation of the individual alkanes, should not be conducted with the technically possible selectivities for economic reasons. The propane fraction which is dehydrogenated in the first reaction zone may therefore definitely also comprise minor residual amounts of butane. Conversely, the dedicated butane dehydrogenation may also be carried out in the presence of residual amounts of propane.

Process step f)—i.e. obtaining the $C_4$ fraction from the dehydrogenation mixture—is carried out in the simplest case with the aid of a distillation column in which the low-boiling constituents of the dehydrogenation mixture ($C_1$ to $C_3$ hydrocarbons, $H_2$, $CO_2$) are withdrawn from the overhead and the $C_4$ fraction is withdrawn from the bottom.

The corresponding process variant is characterized in that the $C_4$ fraction is obtained from the dehydrogenation mixture or dehydrogenation mixtures by distilling the dehydrogenation mixture or dehydrogenation mixtures together, wherein the $C_4$ fraction remains as high boilers and at least one low-boiler fraction is obtained.

The advantage of this procedure is that the low boilers are obtained in the form of a gas at the overhead and therefore may be used also in gaseous form, specifically as fuel gas for heating the dehydrogenation.

If several dedicated reaction zones are provided, several dehydrogenation mixtures are also correspondingly produced therefrom. The low boilers of these dehydrogenation mixtures may be separated together from the $C_4$ fraction in the same column, since outside the reaction zones undesirable subsequent reactions are no longer to be expected. The joint work-up of the dehydrogenation mixtures therefore reduces the apparatus costs.

Figure 2:
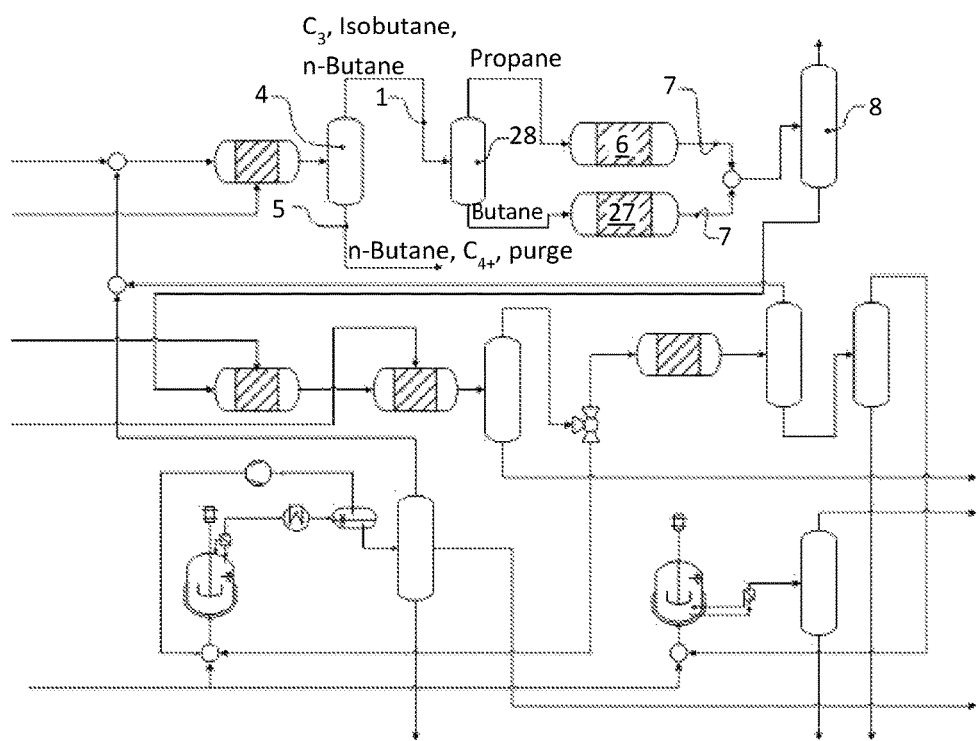
FIG. 2: Process variant with column for separating n-butane and isobutane and also with dedicated $C_3$ and $C_4$ dehydrogenation.
Figure 3:
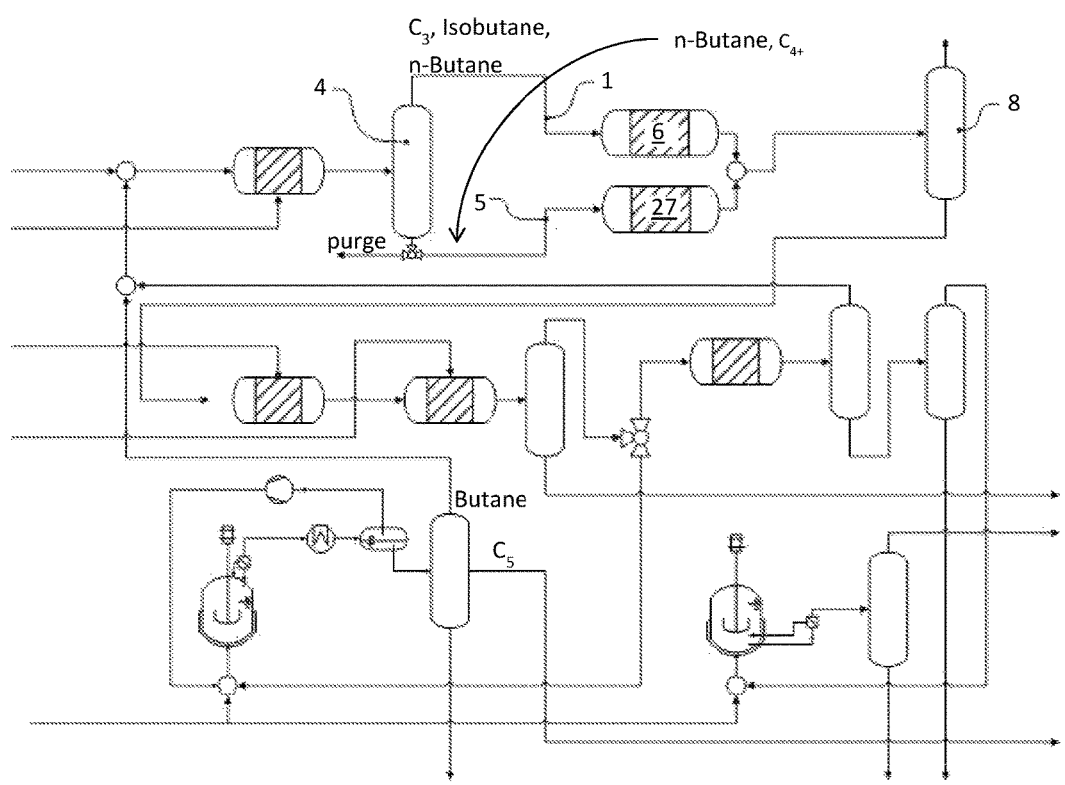
FIG. 3: Process variant with column for separating n-butane and isobutane, with dedicated n-butane dehydrogenation and mixed dehydrogenation of propane and isobutane.
Figure 4:
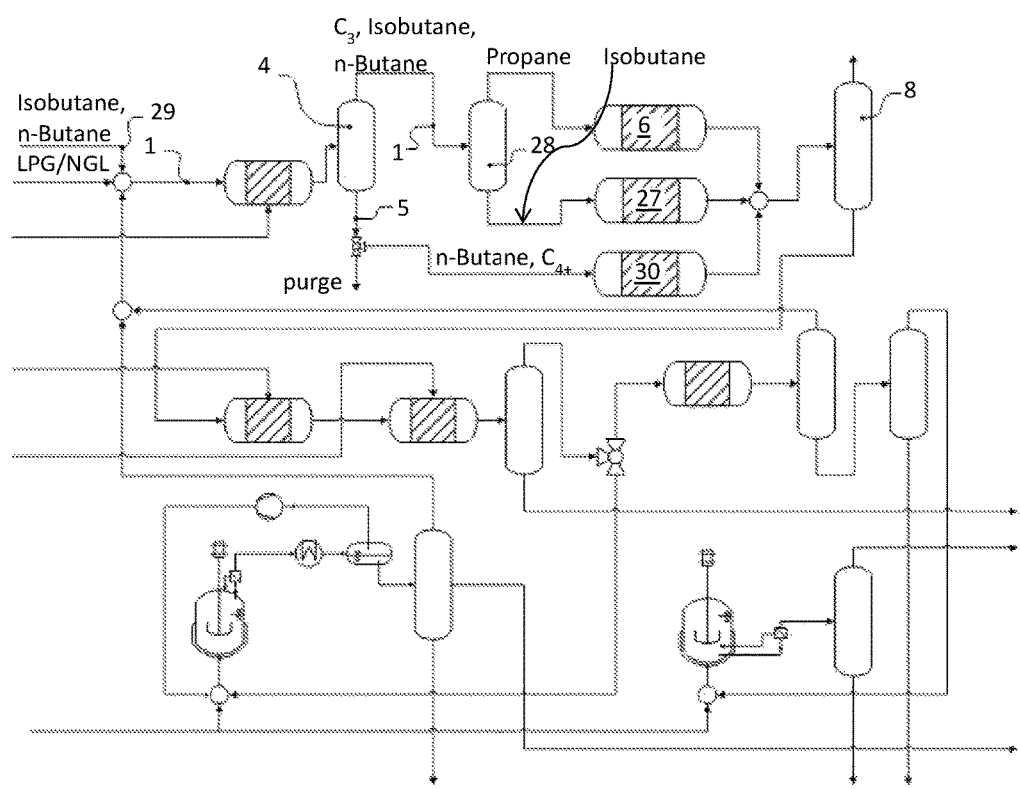
FIG. 4: Process variant with column for separating n-butane and isobutane and also with dedicated dehydrogenation of propane, isobutane and n-butane.
Figure 5:
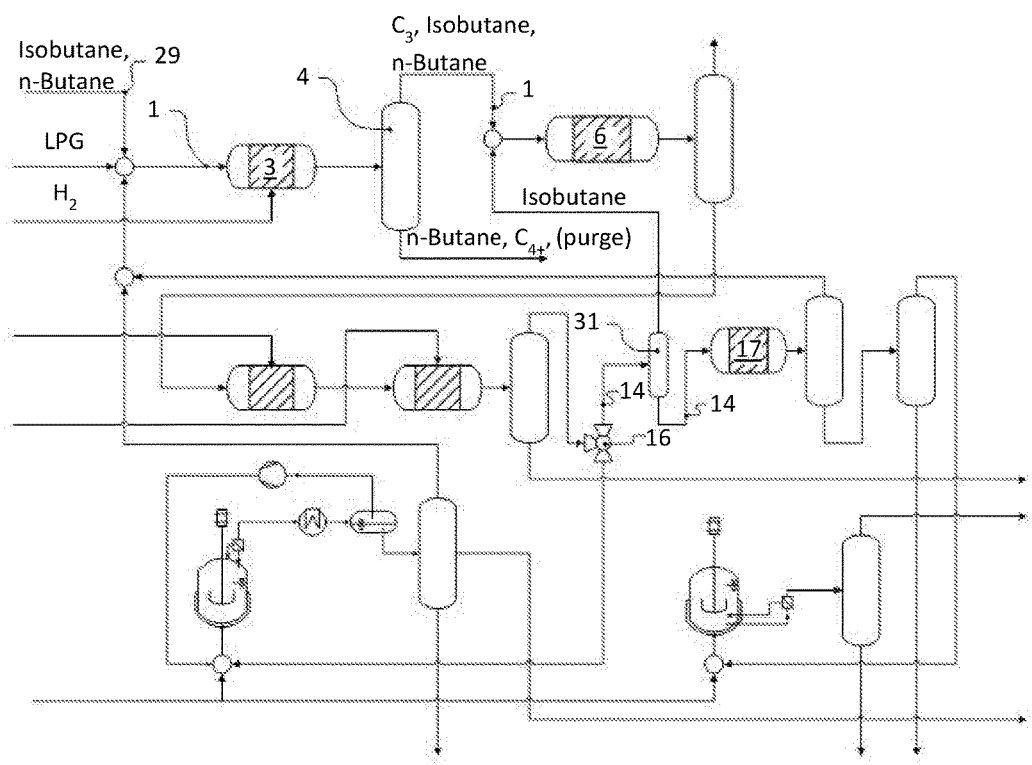
FIG. 5: Process variant with column for separating n-butane and isobutane and also with mixed dehydrogenation and internal isobutane recycling

Some process variants are now to be elucidated with reference to simplified process flow diagrams. The drawings show:

FIG. 1: Basic implementation of the process;

FIG. 2: Process variant with column for separating n-butane and isobutane and also with dedicated $C_3$ and $C_4$ dehydrogenation;

FIG. 3: Process variant with column for separating n-butane and isobutane, with dedicated n-butane dehydrogenation and mixed dehydrogenation of propane and isobutane;

FIG. 4: Process variant with column for separating n-butane and isobutane and also with dedicated dehydrogenation of propane, isobutane and n-butane;

FIG. 5: Process variant with column for separating n-butane and isobutane and also with mixed dehydrogenation and internal isobutane recycling;

At the start, a feed mixture 1 is mixed. For this purpose, LPG is mixed with a return stream 2 from the process essentially comprising butane. Depending on the composition of the LPG used, the feed mixture 1 comprises essentially $C_3$ and/or $C_4$ alkanes. In addition, notable amounts of $C_3$ and $C_4$ olefins may also be present. NGL may also be used instead of LPG, then $C_2$ and $C_5$ hydrocarbons are also present.

In the case that the feed mixture 1 comprises more than 1.0 wt % unsaturated hydrocarbons such as alkenes or alkynes, the unsaturated hydrocarbons content in the feed mixture 1 must be lowered to a value below 1.0 wt %. The reason for this is the sensitivity of the subsequent dehydrogenation to olefins since these cause rapid coking of the catalyst. In order to eliminate the unsaturated compounds, the feed mixture 1 is subjected to a hydrogenation 3 in which the unsaturated compounds are saturated over a heterogeneous catalyst by addition of hydrogen $H_2$. The corresponding alkanes are thus formed from the olefins.

Any catalyst may be used for the hydrogenation which is capable of hydrogenating olefins. Common commercial catalysts use here, for example, Pd, Pt or Ni as active component which has usually been applied to a support composed of $Al_2O_3$ or $SiO_2$. Further components may also be present. There are also mixed systems with Pd and Pt as active component. The support systems may also be mixtures of $Al_2O_3$ together with $SiO_2$. The hydrogenation is effected at elevated pressure with addition of hydrogen generally in a temperature range between 20° C. and 200° C. The hydrogenation can be carried out in the liquid phase or the gas phase, wherein the phase state arises from the regulation of pressure and temperature. Hydrogenation in the liquid phase is advantageous since LPG is supplied as a liquid.

The feed mixture 1 now reaches a distillation column 4 for separating n-butane and isobutane. In the present process used, this column 4 reduces the n-butane content in the feed mixture 1; it is enriched in the bottoms fraction 5 thereof. This comprises, besides n-butane, any further hydrocarbons having more than four carbon atoms $C_{4+}$. The bottoms fraction 5 is discharged from the process (purge). The lower-boiling constituents, especially propane and isobutane, go overhead. Thus the investment and operating costs of the column for separating n-butane and isobutane 4 are not too high and it is less harshly driven such that n-butane also goes overhead.

In principle however, the proportion of n-butane in the bottoms fraction 5 of the column 4 for separating n-butane and isobutane should be greater than the proportion of n-butane in the distilled feed mixture 1 which is withdrawn from the top of the column 4. In the case that the feed mixture comprises hardly any n-butane, column 4 can be dispensed with.

The feed mixture 1 is now subjected to a dehydrogenation. A reaction zone 6 is set up for this purpose which takes the form of a reactor. The reactor comprises a heterogeneous catalyst and is heated with a fuel gas (not shown). Alternatively, an oxidative dehydrogenation can also be provided, whose heat requirement is covered by burning a portion of the feed mixture.

In both cases, a dehydrogenation mixture 7 is withdrawn from the reaction zone. The composition thereof is highly dependent on the feed mixture and the dehydrogenation conditions. Since the saturated bonds are converted into unsaturated bonds in the dehydrogenation (reversed in the hydrogenation), the dehydrogenation mixture comprises in each case the alkenes corresponding to the alkanes present in the feed mixture. However, polyunsaturated compounds may also be present and also by-products and especially the hydrogen released.

A $C_4$ fraction $C_4$ is now separated off from the dehydrogenation mixture 7. The $C_4$ fraction is composed as follows:
  1,3-butadiene: 1 wt % to 5 wt %;
  isobutene: 20 wt % to 50 wt %;
  n-butene: 20 wt % to 50 wt %;
  sum of isobutane and n-butane: 2 wt % to 60 wt %;
  sum of other substances: 0 wt % to 1 wt %;

The $C_4$ fraction $C_4$ is obtained from the dehydrogenation mixture 7 by distilling the dehydrogenation mixture 7, wherein the high boilers form the $C_4$ fraction and a low-boiler fraction 9 is obtained. The low-boiler fraction 9 comprises essentially hydrocarbons having one to three carbon atoms, hydrogen and carbon dioxide. The low-boiler fraction 9 is used as fuel gas for heating the reaction zone 6 (not shown). The overhead product of the second distillation column 8 does not therefore need to be condensed.

If the $C_4$ fraction comprises polyunsaturated compounds such as, in particular, 1,3-butadiene, these should now be removed since these can poison the subsequent catalytic processes, particularly the oligomerization.

A simple hydrogenation is not possible, however, since in this way the butenes only just produced are lost again. Therefore, the $C_4$ fraction is subjected to a so-called selective hydrogenation 10 which selectively converts the 1,3-butadiene but does not hydrogenate the butenes. This is accomplished using special catalysts and addition of CO as moderator.

It is essential now to remove the isobutene from the $C_4$ fraction $C_4$. This is not possible by distillation due to the low boiling point difference compared to 1-butene. For this reason, an MTBE synthesis 11 is provided in which the isobutene is reacted selectively with methanol MeOH to give methyl tert-butyl ether (MTBE). The high-boiling MTBE can now be withdrawn from the bottom of a third distillation column 12 and be discharged. It is suitable especially as a fuel additive but can also be retrocleaved to high-purity isobutene or be used as solvent after further purification. As an alternative to MTBE, the removal may also be effected as ETBE, ethanol being used for this purpose instead of methanol as alcohol.

If the catalyst used in the MTBE synthesis 11 reacts insensitively to polyunsaturated hydrocarbons, the selective hydrogenation 10 may also be arranged downstream of the MTBE synthesis 11.

At the top of the third distillation column 12, an intermediate 13 is taken off. This takes the form of a mixture of $C_4$ hydrocarbons having the following specification:

1,3-butadiene: 0 wt % to 500 ppm by weight;
  isobutene: 0 wt % to 2 wt %;
  n-butene: 30 wt % to 55 wt %;
  sum of isobutane and n-butane: 45 wt % to 70 wt %;
  sum of other substances: 0 wt % to 500 ppm by weight;

The linear $C_4$ olefins 1-butene, cis-2-butene and trans-2-butene, which are collectively referred to as n-butene, form the component of value. Nevertheless, a major portion of less reactive $C_4$ alkanes is also present. The sum total of isobutane and n-butane may even exceed the proportion of linear butenes. Compared to other $C_4$ raw material streams such as crack $C_4$ or FCC $C_4$, the intermediate 13 is noticeably highly diluted with inert alkanes. In contrast, contaminants are hardly present any more.

In accordance with the invention, the intermediate 13 is now divided into two portions 14, 15. This is accomplished in a splitter 16, a simple valve for quantative division without substance separation. The material composition of first portion 14, second portion 15 and intermediate 13 is accordingly identical.

The division into amounts between first and second portion is carried out flexibly according to the prevailing demand situation: if a lot of $C_9$ aldehyde is required (for the production of the plasticizer alcohol isononanol for example), the splitter 16 is adjusted so that the first portion 14 is greater than the second portion 15. If in contrast more $C_5$ or $C_{10}$ aldehyde is required (production of valeraldehyde or of the plasticizer alcohol 2-propylheptanol), the second portion 15 is increased compared to the first portion 14.

The reason for the flexible, demand-oriented division into amounts of the intermediate 13 into its two portions 14 and 15 is that the production chain divides at the splitter 16 into two parallel streams. The first stream is fed with the first portion 14 and the second stream with the second portion 15 of the intermediate 13. The first stream serves for producing $C_9$ aldehyde, whereas the second stream is intended for the $C_5$ or $C_{10}$ production.

For the $C_9$ production, an oligomerization of the $C_4$ olefins to $C_8$ olefins is first required. For this purpose, the first portion 13 is subjected to an oligomerization 17. This is effected in the presence of a solid catalyst comprising amorphous silica/alumina and at least 15% by weight nickel. The nickel content specified refers to elemental nickel. Calculated as nickel oxide, this corresponds to about 20% by weight. A suitable catalyst and preparation thereof is disclosed in U.S. Pat. No. 2,581,228. The oligomerization is effected largely adiabatically, i.e. without heat exchange with the environment via an external coolant. The heat of reaction is discharged with the oligomer 18.

The oligomer 18 is the product of the oligomerization and comprises at least olefins having eight carbon atoms (dimers of butene) and also n-butane and/or isobutane since these substances behave in an inert manner in the oligomerization 17. In addition, the oligomer comprises higher oligomers of butene, for example trimers ($C_{12}$ olefins) and tetramers ($C_{16}$ olefins) of n-butene.

The butanes present in the oligomer 18 and unreacted residual butenes, preferably at a proportion of less than 10% by weight, are now separated off overhead in a fourth column 19 and are reused as return stream 2 in the mixing of feed mixture 1. The butanes thus arrive again in the dehydrogenation and are utilized there in material terms.

The hydrocarbons having more than four carbon atoms $C_{4+}$ present in the oligomer 18 are withdrawn from the bottom of the fourth distillation column. These are almost exclusively olefins. These are further divided in a fifth distillation column 20 into olefins having eight carbon atoms $C_8$ and olefins having more than eight carbon atoms $C_{8+}$. The latter are withdrawn from the bottom of the fifth distillation column 20 and discharged.

The olefins having eight carbon atoms $C_8$ obtained at the head of the fifth distillation column 20 are then reacted together with synthesis gas (syngas, normally a 1:1 mixture of hydrogen and carbon monoxide) in a first hydroformylation 21 to give aldehyde having nine carbon atoms. These are found in a first hydroformylation mixture 22 which is withdrawn from the first hydroformylation 21. Since high-boiling by-products $C_{9+}$ are also formed in the hydroformylation and these are present in the first hydroformylation mixture 22, the first hydroformylation mixture 22 must still be worked up. The work-up takes place in at least one sixth distillation column 23. A first target fraction $C_9$ is obtained at the head thereof, which comprises the desired aldehyde having nine carbon atoms. The high boilers $C_{9+}$ remain in the bottom of the sixth distillation column 23 and are discharged.

Details regarding the $C_8$ hydroformylation and the subsequent product separation can be found in WO2014/131623A1.

The second portion 15 of the intermediate 13 is meanwhile subjected to a second hydroformylation 24 in which aldehydes having five carbon atoms are formed from the n-butene present. A second hydroformylation mixture 25 is obtained in which, besides the desired pentanals, high-boiling by-products $C_{5-}$ are also present.

In a seventh distillation column 26, a second target fraction $C_5$ comprising aldehydes having five carbon atoms is separated from the second hydroformylation mixture 25. The seventh distillation column 26 is here constructed as a side-draw column and the second target fraction C is withdrawn at the side take-off. The non-reactable butanes in the hydroformylation 24 are withdrawn at the head and are reused as return stream 2 in the provision of the feed mixture 1. The high boilers $C_{5+}$ remain in the bottom of the seventh distillation column 26 and are discharged. The $C_5$ aldehydes can be subsequently further processed to give $C_{10}$ aldehydes by means of aldol condensation (not shown).

Details regarding the $C_4$ hydroformylation can be found in WO2014/056732A1. Cross-references for the subsequent product separation and for the aldol condensation are also found therein.

The process variant shown in FIG. 2 differs from the basic variant shown in FIG. 1 in that a dedicated $C_3$ and $C_4$ dehydrogenation is carried out. For this purpose, the first reaction zone 6 is dedicated solely to the propane dehydrogenation and a second reaction zone 27 is provided for the dehydrogenation of $C_4$ alkanes. The operating conditions prevailing in the reaction zones 6, 27 and also the catalysts arranged therein are different.

In order to divide the feed mixture 1 into the two reaction zones, an eighth distillation column 28, which is fed with the overhead product of column 4 (i.e. distilled feed mixture), is arranged directly after the column 4 for separating n-butane and isobutane. The eighth distillation column 28 performs a propane/butane separation. Propane goes overhead into the first reaction zone 6 and butane from the bottom of the eighth distillation column 28 goes into the second reaction zone 27.

The dehydrogenation mixtures each withdrawn from the two reaction zones 6, 27 are combined and worked up together in the second distillation column 8.

The process variant shown in FIG. 3 differs from the basic implementation shown in FIG. 1 in that the n-butane-rich bottoms fraction 5 of the column 4 for separating n-butane and isobutane is partially discharged and is partially fed into a dedicated dehydrogenation which is carried out in a second reaction zone 27. As in FIG. 2, the two dehydrogenation mixtures are further worked up together. In comparison to the process shown in FIG. 2, a propane/butane separation between column 4 and dehydrogenation 6, 27 has been omitted. Instead, a mixed dehydrogenation takes place in the first reaction zone 6.

An important feature of the process shown in FIG. 4 consists in using additionally a second raw material source besides LPG or NGL. In this case it is isobutane and/or n-butane which is fed externally in a stream 29. It may be residues from a further hydroformylation not shown here. This stream is mixed with the LPG or NGL and the butane from the return stream 2 to give the feed mixture 1.

The process shown in FIG. 4 has three dedicated dehydrogenations: In the first reaction zone 6 propane is dehydrogenated, in the second reaction zone 27 primarily isobutane and some n-butane and in the third reaction zone 30 largely n-butane. In order to divide the feed mixture 1 into the three reaction zones 6, 27, 30, two columns are required, namely a column 4 for separating n-butane and isobutane and an eighth distillation column 28 for separating propane/butane. The dehydrogenation mixtures are worked up together.

For the assumed case in FIG. 5, where the feed mixture 1 comprises a great deal of isobutane (for example owing to a corresponding LPG quality or a high isobutane content in stream the 29 from the second raw material source), it is recommended to distill off at least a large portion of the isobutane prior to the oligomerization 17 in order increase the concentration of n-butenes and to utilize the kinetics of the oligomerization in order to obtain higher co-olefin yields.

For this purpose, a ninth distillation column 31 is provided in FIG. 5 which separates off the isobutane overhead from the first portion 13 of the intermediate. It is fed into the reaction zone 6 together with the feed mixture 1 where the dehydrogenation takes place. It is recommended to mix the isobutane with the feed mixture 1 only after the column 4 so that it is not dragged unnecessarily through the hydrogenation 3 and has to be evaporated again in column 4. Incidentally, this process layout corresponds to the basic implementation shown in FIG. 1.

LIST OF REFERENCE SYMBOLS 1 feed mixture
2 return stream (comprising butane)
3 hydrogenation
4 column for separating n-butane and isobutane
5 bottoms fraction
6 reaction zone
7 dehydrogenation mixture
8 second distillation column
9 low-boiler fraction
10 selective hydrogenation
11 MTBE synthesis
12 third distillation column
13 intermediate
14 first portion of the intermediate
15 second portion of the intermediate
16 splitter
17 oligomerization
18 oligomer
19 fourth distillation column
20 fifth distillation column 21 first hydroformylation (from $C_8$ to $C_9$)
22 first hydroformylation mixture
23 sixth distillation column
24 second hydroformylation (from $C_4$ to $C_5$)
25 second hydroformylation mixture
26 seventh distillation column
27 second reaction zone
28 eighth distillation column
29 stream comprising n-butane and isobutane
30 third reaction zone
31 ninth distillation column
$C_4$ $C_4$ fraction
$C_{4+}$ hydrocarbons having more than four carbon atoms
$C_5$ aldehydes having five carbon atoms (second target fraction)
$C_{5+}$ high boilers
$C_8$ olefins having eight carbon atoms
$C_{8+}$ olefins having more than eight carbon atoms
$C_9$ aldehydes having nine carbon atoms (first target fraction)
$C_{9+}$ high boilers
MeOH methanol
MTBE methyl tert-butyl ether
Syngas synthesis gas

The invention claimed is:

1. A process for the flexible preparation of aldehydes having five and nine carbon atoms comprising the following steps:
a) providing a liquid mixture, called LPG or NGL (liquefied petroleum gas or natural gas liquids), which comprises specifically a main component selected from the group consisting of propane, isobutane and n-butane, and at least one secondary component selected from the group consisting of propane, isobutane, n-butane, propene, isobutene or n-butene, with the proviso that the main component selected and the at least one secondary component selected are not identical, and that the mixture has the following composition including the limit values which add up to 100% by weight:
propane: 0 wt % to 50 wt %;
isobutane: 0 wt % to 100 wt %;
n-butane: 0 wt % to 100 wt %;
propene: 0 wt % to 3 wt %;
isobutene: 0 wt % to 10 wt %;
n-butene: 0 wt % to 15 wt %;
sum of other substances: 0 wt % to 5 wt %;
b) mixing a feed mixture using the LPG or NGL;
c) in the case that the feed mixture comprises more than 1.0% by weight unsaturated hydrocarbons: reducing the content of unsaturated hydrocarbons in the feed mixture to a value below 1.0% by weight by subjecting the feed mixture to a hydrogenation;
d) optionally: reducing the n-butane content of the feedstock mixture by distillation of the feed mixture to obtain a bottoms fraction comprising n-butane, wherein the proportion of n-butane in the bottoms fraction comprising n-butane is greater than the proportion of n-butane in the distilled feed mixture;
e) dehydrogenating the feed mixture to obtain at least one dehydrogenation mixture,
f) obtaining a C4 fraction from the dehydrogenation mixture, wherein the C4 fraction has the following composition including the limit values which add up to 100% by weight:
1,3-butadiene: 1 wt % to 5 wt %;
isobutene: 20 wt % to 50 wt %;
n-butene: 20 wt % to 50 wt %;
sum of isobutane and n-butane: 2 wt % to 60 wt %;
sum of other substances: 0 wt % to 1 wt %;
g) at least partial removal of 1,3-butadiene and isobutene from the C4 fraction to obtain an intermediate which has the following composition including the limit values which add up to 100% by weight:
1,3-butadiene: 0 wt % to 500 ppm by weight;
isobutene: 0 wt % to 2 wt %;
n-butene: 30 wt % to 55 wt %;
sum of isobutane and n-butane: 45 wt % to 70 wt %;
sum of other substances: 0 wt % to 500 ppm by weight;
h) dividing the intermediate into a first portion and a second portion in a splitter;
i) optionally reducing the isobutane content of the first portion of the intermediate by distillation of the first portion of the intermediate to obtain a bottoms fraction comprising isobutane, wherein the proportion of isobutane in the bottoms fraction comprising isobutane is greater than the proportion of isobutane in the first portion of the intermediate distilled and using the bottoms fraction comprising isobutane to increase the isobutane content of the feed mixture in which the bottoms fraction comprising isobutane is added to the feed mixture or is used when mixing the feed mixture;
j) subjecting the first portion of the intermediate to an oligomerization in the presence of a solid catalyst comprising amorphous silica/alumina and at least 15% by weight nickel, whereby an oligomer is obtained comprising olefins having eight carbon atoms and butane,
k) separating butane from the oligomer and using the butane separated when mixing the feed mixture;
l) separating olefins having eight carbon atoms from the oligomer and pressurizing the separated olefins having eight carbon atoms with synthesis gas for the purpose of carrying out a first hydroformylation to obtain a first hydroformylation mixture comprising at least aldehydes having nine carbon atoms;
m) separating a first target fraction comprising aldehydes having nine carbon atoms from the first hydroformylation mixture;
n) pressurizing the second portion of the intermediate with synthesis gas for the purpose of carrying out a second hydroformylation to obtain a second hydroformylation mixture comprising at least aldehydes having five carbon atoms and also butane;
o) separating butane from the second hydroformylation mixture and using the butane separated when mixing the feed mixture; and
p) separating a second target fraction comprising aldehydes having five carbon atoms from the second hydroformylation mixture
wherein the first hydroformylation of step l) and the second hydroformylation of step n) are arranged in parallel, and not arranged serially.

2. The process according to claim 1, wherein the intermediate is divided into the first portion and the second portion considering the changing need over time for aldehyde having nine carbon atoms and aldehyde having five carbon atoms in such a way that the ratio of the first portion to the second portion changes analogously with time to the change over time of the ratio of the need for aldehyde having nine carbon atoms to the need for aldehyde having five carbon atoms.

3. The process according to claim 1, wherein the oligomer also comprises unreacted olefins having four carbon atoms, wherein unreacted olefins having four carbon atoms are separated from the oligomer and are fed into the oligomerization together with fresh intermediate.

4. The process according to claim 3, wherein the oligomerization is conducted in a reaction zone, wherein more than 60% up to at most 90% of the heat of reaction resulting from the oligomerization is removed from the reaction zone with the oligomer (partially adiabatic reaction regime).

5. The process according to claim 3, wherein the oligomerization is conducted in a reaction zone, wherein more than 90% up to at most 100% of the heat of reaction resulting from the oligomerization is removed from the reaction zone with the oligomer (adiabatic reaction regime).

6. The process according to claim 1, wherein the intermediate is obtained by subjecting the $C_4$ fraction to a selective hydrogenation in order to at least partially remove 1,3-butadiene present in the $C_4$ fraction by hydrogenation.

7. The process according to claim 6, wherein the intermediate is obtained, before or after carrying out the selective hydrogenation, by reacting the isobutene present in the $C_4$ fraction with an alcohol at least partially to give an ether and removing the ether formed in this case at least partially by distillation.

8. The process according to claim 1, wherein additionally isobutane and/or n-butane is used when mixing the feed mixture, which does not originate from the LPG or NGL provided nor from the oligomer or from the second hydroformylation mixture.

9. The process according to claim 1, wherein the dehydrogenation is effected at least partially without addition of an oxidizing agent.

10. The process according to claim 1, wherein the dehydrogenation of the feed mixture is conducted in a reaction zone, wherein the alkanes having three and four carbon atoms present in the feed mixture are dehydrogenated together in the same reaction zone.

11. The process according to claim 1, wherein the dehydrogenation of the feed mixture is conducted in at least two reaction zones, wherein alkanes having three carbon atoms present in the feed mixture are dehydrogenated in the first reaction zone and wherein alkanes having four carbon atoms present in the feed mixture are dehydrogenated in the second reaction zone.

12. The process according to claim 10, in which the n-butane content of the feed mixture is reduced by distillation of the feed mixture to obtain a bottoms fraction comprising n-butane such that the proportion of n-butane in the bottoms fraction comprising n-butane is greater than the proportion of n-butane in the distilled feed mixture, characterized in that a further reaction zone is provided in which the the distilled feed mixture is not dehydrogenated whereas the bottoms fraction comprising n-butene is subjected to a dehydrogenation in the further reaction zone.

13. The process according to claim 1, wherein the $C_4$ fraction is obtained from the dehydrogenation mixture or dehydrogenation mixtures by distilling the dehydrogenation mixture or dehydrogenation mixtures together, wherein the $C_4$ fraction remains as high boilers and at least one low-boiler fraction is obtained.

14. The process according to claim 1, wherein the LPG (liquefied petroleum gas) provided has the following composition including the limit values adding up to 100% by weight:
propane: 0 wt % to 3 wt %;
isobutane: 20 wt % to 80 wt %;
n-butane: 20 wt % to 80 wt %;
propene: 0 wt % to 3 wt %;
isobutene: 0 wt % to 10 wt %;
n-butene: 0 wt % to 15 wt %;
sum of other substances: 0 wt % to 5 wt %.

15. The process according to claim 1, wherein the LPG (liquefied petroleum gas) provided has the following composition including the limit values adding up to 100% by weight:
propane: 10 wt % to 40 wt %;
isobutane: 15 wt % to 85 wt %;
n-butane: 15 wt % to 85 wt %;
propene: 0 wt % to 3 wt %;
isobutene: 3 wt % to 10 wt %;
n-butene: 2 wt % to 15 wt %;
sum of other substances: 0 wt % to 5 wt %.

16. The process according to claim 1, wherein the NGL (natural gas liquids) provided has the following composition including the limit values adding up to 100% by weight:
ethane: 0 wt % to 2 wt %;
propane: 0 wt % to 50 wt %;
isobutane: 0 wt % to 100 wt %;
n-butane: 0 wt % to 100 wt %;
propene: 0 wt % to 3 wt %;
isobutene: 0 wt % to 10 wt %;
n-butene: 0 wt % to 15 wt %;
pentane: 0 wt % to 2 wt %;
sum of other substances: 0 wt % to 1 wt %.

17. The process according to claim 2, wherein the LPG (liquefied petroleum gas) provided has the following composition including the limit values adding up to 100% by weight:
propane: 0 wt % to 3 wt %;
isobutane: 20 wt % to 80 wt %;
n-butane: 20 wt % to 80 wt %;
propene: 0 wt % to 3 wt %;
isobutene: 0 wt % to 10 wt %;
n-butene: 0 wt % to 15 wt %;
sum of other substances: 0 wt % to 5 wt %.

18. The process according to claim 2, wherein the LPG (liquefied petroleum gas) provided has the following composition including the limit values adding up to 100% by weight:
propane: 10 wt % to 40 wt %;
isobutane: 15 wt % to 85 wt %;
n-butane: 15 wt % to 85 wt %;
propene: 0 wt % to 3 wt %;
isobutene: 3 wt % to 10 wt %;
n-butene: 2 wt % to 15 wt %;
sum of other substances: 0 wt % to 5 wt %.

19. The process according to claim 2, wherein the NGL (natural gas liquids) provided has the following composition including the limit values adding up to 100% by weight:
ethane: 0 wt % to 2 wt %;
propane: 0 wt % to 50 wt %;
isobutane: 0 wt % to 100 wt %;
n-butane: 0 wt % to 100 wt %;
propene: 0 wt % to 3 wt %;
isobutene: 0 wt % to 10 wt %;
n-butene: 0 wt % to 15 wt %;
pentane: 0 wt % to 2 wt %;
sum of other substances: 0 wt % to 1 wt %.

20. The process according to claim 2, wherein the oligomer also comprises unreacted olefins having four carbon atoms, wherein unreacted olefins having four carbon atoms are separated from the oligomer and are fed into the oligomerization together with fresh intermediate.

* * * * *